United States Patent [19]
Lin et al.

[11] Patent Number: 5,871,927
[45] Date of Patent: Feb. 16, 1999

[54] NUCLEOTIDE ANALOG-CONTAINING HYBRID SUBTRACTION WITH SEQUENTIALLY ENZYMATIC DIGESTION

[76] Inventors: Shi-Lung Lin, 400 N. Chapel Ave., #114, Alhambra, Calif. 91801; Shao-Yao Ying, 1953 Wellesley Rd., San Marino, Calif. 91108

[21] Appl. No.: 854,400

[22] Filed: May 12, 1997

[51] Int. Cl.$^6$ .............................. C12Q 1/68; C12P 19/34
[52] U.S. Cl. .............................................. 435/6; 435/91.2
[58] Field of Search ............................... 435/6, 91.2, 810

[56] References Cited

U.S. PATENT DOCUMENTS

| 5,500,356 | 3/1996 | Li et al. ................................. 435/91.1 |
| 5,525,471 | 6/1996 | Zeng ............................................. 435/6 |
| 5,565,340 | 10/1996 | Chenchik et al. ..................... 435/91.2 |

OTHER PUBLICATIONS

Bjourson et al., "Combined Subraction Hybridization . . . Sequences", *Applied and Environmental Microbiology* 58:2296–2301 (1992).
Chang et al., "Cloning and Expression of a Gamma–Inferon–inducible Gene . . . " *International Immunology;* 1–388–397 (1989).
Coochini et al., "Identification of Genes . . . " *Nucleic Acids Res.* 5742–5747 (1993).
Davis et al., "Expression of a Single Transfected cDNA . . . " *Cell* 51:987–1000 (1987).
Duguid et al., "Library Subtraction . . . ", *Nucleic Acids Res.* 18:2789–2792 (1990).
Kunkel et al., Specific Cloning . . . *Proc. Natl Acad. Sci USA* 82,4778–4782 (1985).
Lamar et al. *Cell* 37: 171–177 (1984).
Lehninger et al., "Principles of Biochemistry . . . ", Worth Press, pp. 342–343 (1993).
Lisitsyn et al., "Cloning the Differences . . . " *Science* 259:946–951 (1993).
Littman et al., "The Isolation and Sequence of the Gene. . . " *Cell* 40: 237–246 (1985).
Maddon et al., "The Isolation and Nucleotide . . . " *Cell* 42:93–104 (1985).
Nussbaum et al., *Proc. Natl Acad. Sci USA* 84:6521–6525 (1987).
Sambrook et al, *"Molecular Cloning, 2nd Ed."*, Cold Spring Harbor Laboratory Press, p.10.45 (1989).
Stras et al., "Genomic Subraction . . . " *Proc. Natl Acad. Sci USA* 87:1889–1893 (1990).
Wang et al., "A gene Expression Screen", *Proc. Natl Acad. Sci USA* 88:11505–11509 (1991).
Wicland et al., "A Method for Difference Cloning . . ." *Proc. Natl. Acad. Sci USA* 87:2720–2724 (1990).
Gubler et al., "A Simple and Very Efficient Method . . ." *Gene* 25: pp. 263–269 (1983).

*Primary Examiner*—Kenneth R. Horlick
*Attorney, Agent, or Firm*—Thomas I. Rozsa; Tony D. Chen

[57] ABSTRACT

The present invention provides a method for fast, simple, and reliable isolation of desired different sequences from two DNA libraries. Excess amount of nucleotide analog-containing DNA subtracter from control cells is generated by incorporating nucleotide analog with a template-dependent extension reaction to introduce susceptible-sites for subsequent enzymatic digestion. Hybridization of the control subtracter and experimental DNA is performed with a heat-melting and then cool-reassociation technique. The hybridized DNAs are subtracted with nucleotide analog-removing enzyme first, resulting in nicking or gapping all nucleotide analog-containing hybrid duplexes which are further digested by single-strand-specific nuclease. Desired DNA sequences from the experimental cells, but not the control ones stay intact throughout the digestion procedure and can be selectively amplified at the end. This technique is designed for the subtractive hybridization of different sequences between two DNA libraries from distinct cell sources and will allow more efficient isolations in experiments on cancer formation, development of gene therapy, and understanding of pathological status and developmental regulation.

53 Claims, 15 Drawing Sheets

FIG.1(b)

```
4. ABASIC SITE GENERATION:
   ANALOG-REMOVING ENZYME DIGESTION.
```

```
5. DIGESTION OF SURPLUS SUBTRACTER AND
   HOMOLOGY IN THE ABASIC SITES:
   NUCLEASE S1 DIGESTION.
```

```
6. SELECTIVE AMPLIFICATION:
   HIGH-ANNEALING-TEMPERATURE PCR
```

```
7. DISPLAY OF HETEROLOGOUS DNA RESULTS:
   ELECTROPHORESIS ON GEL.
```

DIFFERENT DNAs PRESENT IN THE
EXPERIMENTAL SET, BUT ALMOST
ABSENT IN THE CONTROL SET

```
8. VERIFICATION OF THE RESULTS:
   NORTHERN BLOTTING ASSAY; CLONING; AND
   SEQUENCING.
```

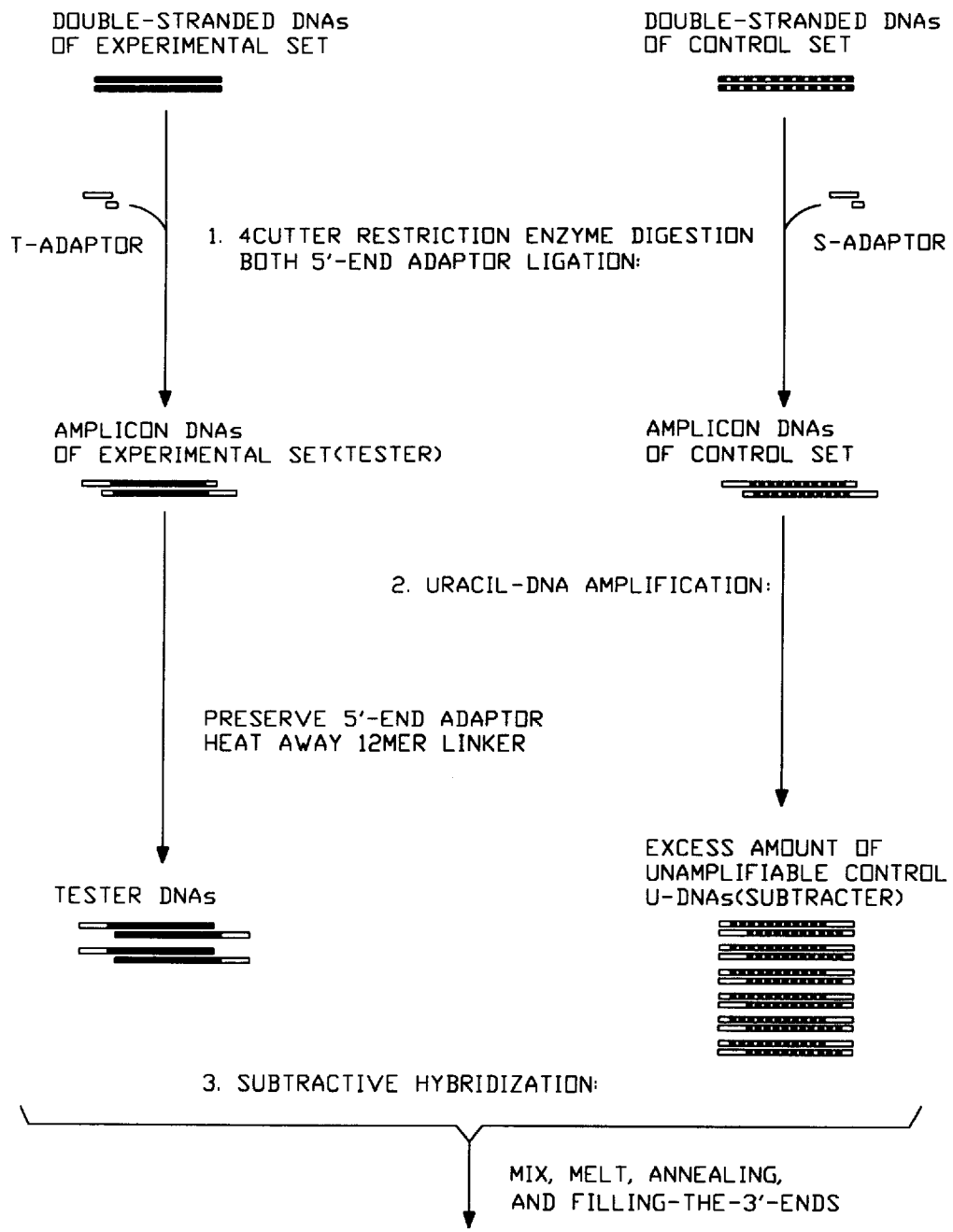
FIG.3(a) WHEN TESTER-ADAPTOR IS DIFFERENT FROM SUBTRACTER-ADAPTOR:

FIG.3(b)

TESTER-HOMOHYBRIDS:
HETEROLOGOUS DNAs

TESTER-SUBTRACTER
HETEROHYBRIDS:
HOMOLOGOUS DNAs

SURPLUS SUBTRACTERS
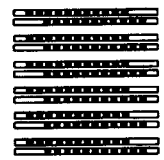

4. URACIL-DNA GLYCOSYLASE DIGESTION:
5. NUCLEASE S1 DIGESTION:

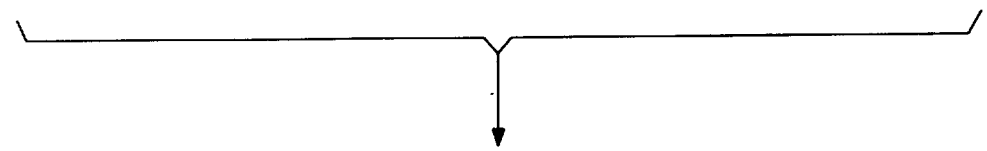

DIFFERENT DNAs
FROM TESTERS

ELIMINATED HOMOLOGY    ELIMINATED SUBTRACTERS

6. SELECTIVE AMPLIFICATION:

T-PRIMER ━   HIGH-ANNEALING-TEMPERATURE
POLYMERASE CHAIN REACTION

HETEROLOGOUS DNAs

NO AMPLIFICATION    NO AMPLIFICATION

EXPONENTIAL
AMPLIFICATION

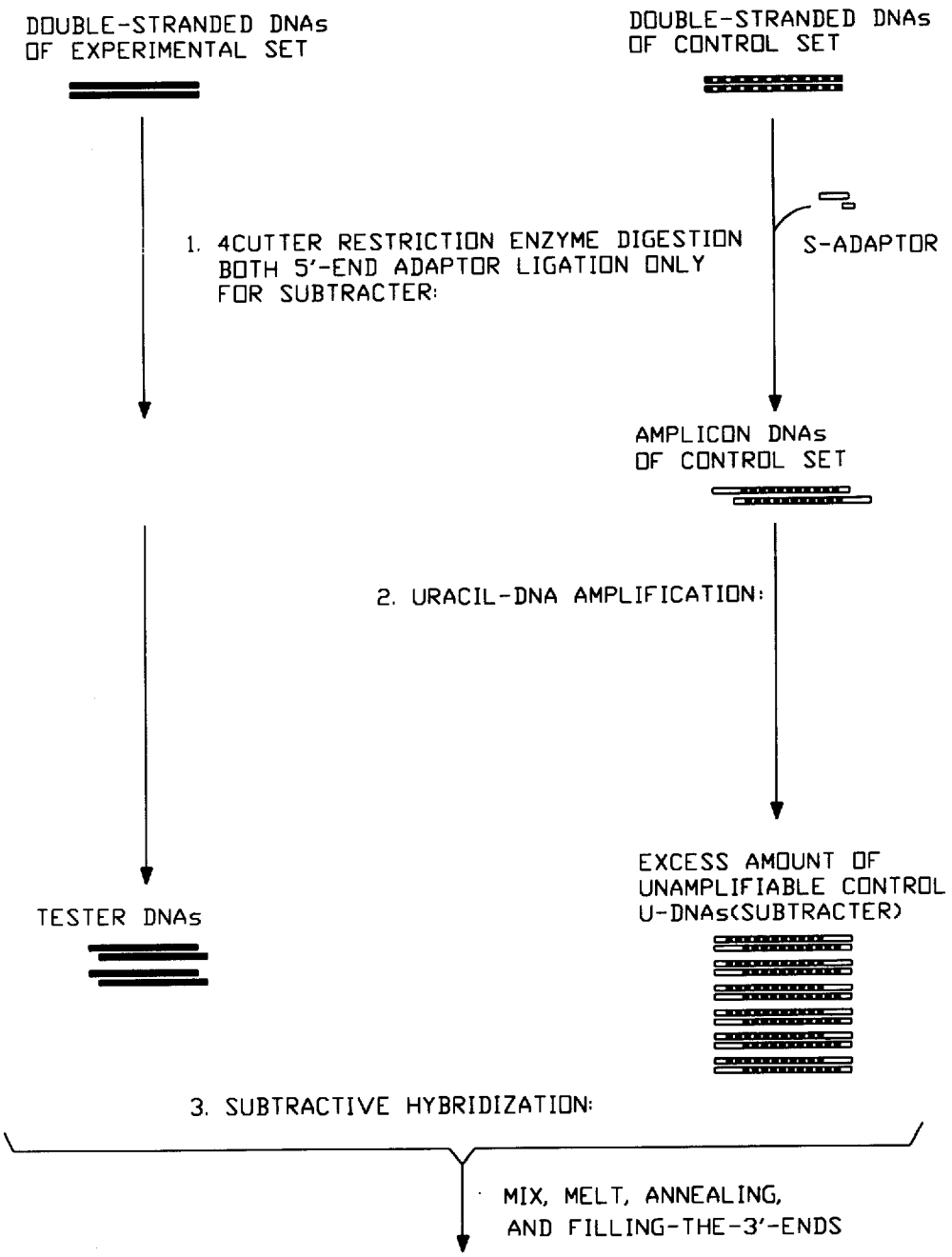

FIG.5(a)

EXPERIMENTAL DNAs
WITH 5'-ADAPTOR(TESTERS)

EXCESS AMOUNT OF
CONTROL N-DNAs
(SUBTRACTERS)

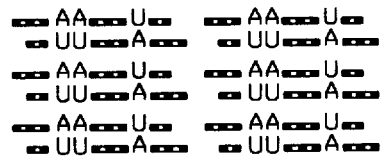

3. SUBTRACTIVE HYBRIDIZATION:

MIX, MELT, ANNEALING,
AND FILLING-THE-3'-ENDS

TESTER-HOMOHYBRIDS:

TESTER-SUBTRACTER
HETEROHYBRIDS:

SURPLUS SUBTRACTERS

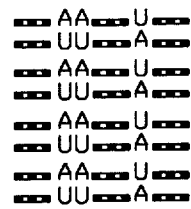

4. NUCLEOTIDE ANALOG-REMOVING ENZYME DIGESTION

INTACT HETEROLOGOUS
TESTER-HOMOHYBRIDS

NICKED-AND GAPPED-
HOMOLOGY HETEROHYBRIDS

NICKED-AND GAPPED-
SURPLUS SUBTRACTERS

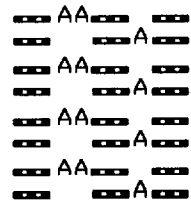

5. NUCLEASE S1 DIGESTION:

FIG.5(b)

INTACT HETEROLOGOUS        NICK/GAP-DIGESTED         NICK/GAP-DIGESTED
DNAs FROM TESTERS          HOMOLOGY FRAGMENTS        SUBTRACTER FRAGMENTS

                                     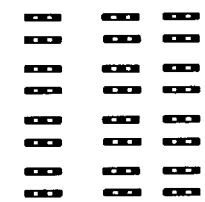

6. SELECTIVE AMPLIFICATION:

SPECIFIC TESTER-PRIMER ⊂ ⟍    HIGH-ANNEALING-TEMPERATURE
                               POLYMERASE CHAIN REACTION

HETEROLOGOUS DNAs          HOMOLOGOUS DNAs           SURPLUS SUBTRACTERS
                           (COMMON SEQUENCES)

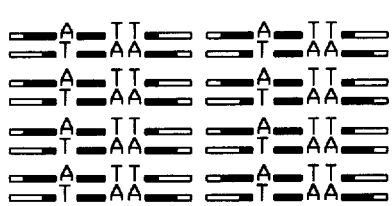             NO AMPLIFICATION          NO AMPLIFICATION

EXPONENTIAL
AMPLIFICATION

TABLE 1

| NAME | APPLICATION | SEQUENCE |
|---|---|---|
| 9. T-DPN2-24MER | 5'-LIGATION ADAPTOR; PCR SPECIFIC PRIMER FOR TESTER GENOMIC DNA. | 5'-GCCACCAGAAGAGCGTGTACGCCA-3' |
| 10. T-DPN2-12MER | 5'-LIGATION LINKER FOR TESTER GENOMIC DNA. | 5'-GATCTGGCGTAC-3' (5'-DEPHOSPHORYLATED) |
| 11. S-DPN2-24MER | 5'-LIGATION ADAPTOR; PCR SPECIFIC PRIMER FOR SUBTRACTER GENOMIC DNA. | 5'-CGGUAGUGACUCGGUUAAGAUCGA-3' |
| 12. S-DPN2-12MER | 5'-LIGATION LINKER FOR SUBTRACTER GENOMIC DNA. | 5'-GAUCUCGAUCUU-3' (5'-DEPHOSPHORYLATED) |
| 13. T-HPA2-24MER | 5'-LIGATION ADAPTOR; PCR SPECIFIC PRIMER FOR TESTER cDNA. | 5'-GCCACCAGAAGAGCGTGTACGTCC-3' |
| 14. T-HPA2-11MER | 5'-LIGATION LINKER FOR TESTER cDNA. | 5'-CGGGACGTACA-3' (5'-DEPHOSPHORYLATED) |
| 15. S-HPA2-24MER | 5'-LIGATION ADAPTOR; PCR SPECIFIC PRIMER FOR SUBTRACTER cDNA. | 5'-CGGUAGUGACUCGGUUAAGAUCGC-3' |
| 16. S-HPA2-11MER | 5'-LIGATION LINKER FOR SUBTRACTER cDNA. | 5'-CGGCGAUCUUA-3' (5'-DEPHOSPHORYLATED) |

NUCLEOTIDE ANALOG-CONTAINING HYBRID SUBTRACTION WITH SEQUENTIALLY ENZYMATIC DIGESTION

BACKGROUND OF THE INVENTION

1. Field of the Invention

The present invention generally relates to the field of methods for isolating specific DNA sequences. More particularly, the present invention relates to the field of improved methods of rapid isolation of differentially expressed genes or deleted/inserted sequences in genomic DNA through subtractive hybridization with nucleotide analog-containing subtracter and sequentially enzymatic digestion.

2. Description of the Prior Art

The following references are pertinent to this invention:

1. Bjourson et. al., "Combined Subtraction Hybridization and Polymerase Chain Reaction Amplification Procedure for Isolation of Strain-specific Rhizobium DNA Sequences", *Applied and Environmental Microbiology* 58: 2296–2301 (1992);
2. Chang et. al., "Cloning and Expression of a Gamma-interferon-inducible Gene in Monocytes: a New Member of a Cytokine Gene Family", *International Immunology* 1:388–397 (1989);
3. Coochini et. al.,"Identification of Genes Up-regulated in Differentiating Nicotania glauca Pith Tissue, Using an Improved Method for Construction a Subtractive cDNA Library", *Nucleic Acids Res.* 21: 5742–5747 (1993);
4. Davis et. al., "Expression of a Single Transfected cDNA Converts Fibroblasts to Myoblasts", *Cell* 51: 987–1000 (1987);
5. Duguid et. al., "Library Subtraction of In Vitro cDNA Libraries to Identify Differentially Expressed Genes in Scapic Infection", *Nucleic Acids Res.* 18: 2789–2792 (1990);
6. Kunkel et. al., "Specific Cloning of DNA Fragments Absent from the DNA of a Male Patient with an X Chromosome Deletion", *Proc. Natl. Acad. Sci. USA* 82, 4778–4782 (1985);
7. Lamar et. al., "Y-encoded, Species-specific DNA in Mice: Evidence that the Y Chromosome exists in Two Polymorphic Forms in Inbred Strains," *Cell* 37:171–177 (1984);
8. Lehninger et. al., *"Principles of Biochemistry, 2nd Edition "*, Worth Press, pp342–343 (1993);
9. Lisitsyn et. al., "Cloning the Differences Between Two Complex Genomes", *Science* 259: 946–951 (1993);
10. Littman et. al., "The Isolation and Sequence of the Gene Encoding T8: a Molecule Defining Functional Classes of T Lymphocytes", *Cell* 40: 237–246 (1985);
11. Maddon et. al., "The Isolation and Nucleotide Sequence of a cDNA Encoding the T Cell Surface Protein T4: a New Member of the Immunoglobulin Gene Family", *Cell* 42: 93–104 (1985);
12. Nussbaum et. al., "Isolation of Anonymous DNA Sequences from within a Submicroscopic X Chromosomal Deletion in a Patient with Choroideremia, Deafness, and Mental Retardation," *Proc. Natl. Acad. .Sci. USA* 84: 6521–6525 (1987);
13. Sambrook et. al., *"Molecular Cloning, 2nd Edition"*, Cold Spring Harbor Laboratory Press, p10.45 (1989);
14. Straus et. al., "Genomic Subtraction for Cloning DNA Corresponding to Deletion Mutations", *Proc. Natl. Acad. Sci. USA* 87: 1889–1893 (1990);
15. Wang et. al., "A gene Expression Screen", *Proc. Natl. Acad. Sci. USA* 88: 11505–11509 (1991);
16. Wicland et. al., "A Method for Difference Cloning; Gene Amplification Following Subtractive Hybridization", *Proc. Natl. Acad. Sci. USA* 87: 2720–2724 (1990);
17. Ueli et. al., "A Simple and Very Efficient Method for Generating cDNA Libraries", *Gene,* 25: pp263–269 (1983); and
18. U.S. Pat. No. 5,525,471 issued to Zeng Jin on Jun. 11, 1996 for "Enzymatic Degrading Subtraction Hybridization".

The ability to compare two different DNA libraries has permitted inquiries into the role of differentially expressed genes or deleted-/inserted-genomic sequences involving the mechanisms of neoplastic transformation, developmental regulation, therapeutic effect, pathological disorder, and cell-physiological phenomena. Understanding the alterations of gene expression and chromosomal rearrangement between normal and disordered cells is especially important for gene therapy, eugenical improvement, pharmaceutical design and etiological investigations.

Several methods have been designed to detect and isolate different DNA sequences which are present in one DNA library but absent in another one. One of the most commonly used methods to accomplish such purpose is subtractive hybridization, involving the elimination of homologous (common) sequences from the mixture of two mutually compared DNA libraries. This kind of selective isolation can be done either between two cDNA libraries (Davis et. al., *Cell* 51: 987–1000 (1987)), or between two genomic DNA libraries (Lamar et. al., *Cell* 37: 171–177 (1984)). In brief, this method relies upon the generation of double-stranded DNA libraries from both control cells (subtracter DNA) and cells after treatment, disorder or change (tester DNA). The two DNA libraries are then denatured and hybridized to each other, resulting in subtracter-tester duplex formation if a sequence is common to both DNA populations. By removing the subtracter and common sequence, the remaining DNA is the different sequence which is only present in the tester and also highly related to the treatment, disorder or change of interest.

Subtractive hybridization has been successfully used in the discovery of many functional genes and crucial genomic loci, such as $T_4$ and $T_8$ lymphocyte-surface glycoproteins (Maddon et. al., *Cell* 42: 93–104 (1985); Littman et. al., *Cell* 40: 237–246 (1985)), gamma-interferon-induced cytokines in monocytes (Chang et. al., *International Immunology* 1:388–397 (1989)), choroidermia loci (Nussbaum et. al., *Proc. Natl. Acad. Sci. USA* 84: 6521–6525 (1987)), Duchenne muscular dystrophy-related loci (Kunkel et. al., *Proc. Natl. Acad. Sci. USA* 82, 4778–4782 (1985)), and human Y-chromosome-specific DNA (Lamar, 1984).

In some cases, the isolated DNA is so abundant in a cell source that it can be detected directly without prior enrichment. In most cases, however, the small amount of desired DNA requires that it be amplified by the polymerase-chain-reaction (PCR), which allows a strengthened observation after multiple cycles of subtractive hybridization (Wang et. al., *Proc. Natl. Acad. Sci. USA* 88: 11505–11509 (1991); Coochini et. al., *Nucleic Acids Res.* 21: 5742–5747 (1993)). Additionally, PCR amplification can be used to enrich both subtracter and tester libraries when starting material is limited (Wicland et. al., *Proc. Natl. Acad. Sci. USA* 87: 2720–2724 (1990)). In short, such amplification is achieved by ligating a specific adaptor to the both ends of an endonuclease-restricted DNA library (amplicon DNA), resulting in the generation of a primer-conjugated region for PCR. However, the PCR amplification may also cause non-specific subtracter contamination when a multiple subtraction/amplification procedure is applied.

Using biotinylation of the subtracter DNA has been widely used to increase subtraction specificity with streptavidin-containing chromatography and to reduce the amount of subtracter needed for hybridization. Straus et. al. (*Proc. Natl. Acad. Sci. USA* 87: 1889–1893 (1990)) used biotinylated-deletion-mutant genomic DNAs to hybridize with restricted-wild type genomic DNAs, then subtracted the undesired hybrid with avidin-coated beads. The unbound sequences were ligated to specific adaptor and amplified by PCR, resulting in a finding of genomic deletions present in the mutant but absent in the wild type. Meanwhile, Duguid et. al. (*Nucleic Acids Res.* 18: 2789–2792 (1990)) performed a similar experiment but using a biotinylated double-stranded cDNA library of a normal hamster brain to hybridize with a non-modified cDNA library of a scrapie-infected hamster brain, generating biotinylated complexes which were removed by a biotin-binding avidin resin. The cDNAs remaining in the suspension were amplified and confirmed as scrapie-infected specific gene sequences. Based on experiments like these, it is noteworthy that most previous methods require several cycles of subtractive hybridization because of the incomplete nature of the biotin-avidin affinity interaction. That means: although these methods can successfully reduce the amplification-potential of subtracter DNA, the inevitable use of biotinylation and multiple precipitation/chromatography causes an increase of tedious laboratory-work and a potential loss of desired sequences during repeated subtraction steps.

Bjourson et. al. (*Applied and Enviromental Microbiology* 58: 2296–2301 (1992)) reported a further improvement in subtractive hybridization methods that employed a biotinylated primer and a uracil-containing deoxynucleotide mixture (e.g. mixture of dATP, dCTP, dGTP and dUTP) to generate uracil-containing DNA (U-DNA) subtracter in PCR. In this case, control and experimental DNA libraries were isolated from different strains of *Rhizobium leguminosarum*, restricted by an endonuclease, and ligated to different specific adaptors. After that, a special PCR, called uracil-incorporation PCR, was performed to produce the biotinylated subtracter U-DNA which was then hybridized with relatively limited amount of non-modified experimental DNAs, resulting in the formation of biotinylated heterohybrids that contained homologous sequences common to both libraries. Since the biotinylated sequence was removed by streptavidin-phenol-chloroform extraction and the surplus U-DNA was digested with uracil-DNA glycosylase (UDG), the remaining DNAs should be the strain-specific sequences. However, this method still required tedious work in biotinylation and at least two rounds of extraction and chromatography.

Prior art attempts at simplifying subtraction with enzymatic digestion, such as U.S. Pat. No. 5,525,471 to Jin, uses a two-exonuclease degradation precedure. Tester cDNA (from experimental cells) is modified by the incorporation of deoxynucleoside thiotriphosphates which protects the tester from digestion by a first exonuclease. After the tester is hybridized with a non-modified subtracter cDNA (from control cells), the surplus subtracter homohybrid and the entire subtracter-half of the tester-subtracter heterohybrid are digested by the first exonuclease. Before the single-stranded tester half of the heterohybrid can reassociate with each other, a second exonuclease digests all single-stranded tester sequences. This can give a quick, simple way to achieve subtractive hybridization, but it also generates some other problems. First, the property of the desired tester sequence is altered by the modifications which may hinder subsequent analysis. Second, a small amount of reassociation of the single-stranded-tester may occur before the second digestion, resulting in an increase of false-positive results. Third, a long-term, two-exonuclease degradation may damage the small amount of desired sequences, resulting in an increase of false-negative results.

In summary, it is desirable to have a fast, simple, and reliable subtractive hybridization method for distinguishing different sequences from two cDNA or genomic DNA libraries, of which the differences may contribute to developing a therapy for diseases, a diagnosis for inherent problems, or a design for genetic engineering.

SUMMARY OF THE INVENTION

The present invention is a novel subtractive hybridization method which provides a fast, simple, and reliable isolation of desired different sequences from either cDNA or genomic DNA libraries.

Described in detail, a preferred embodiment of the present invention method includes the following steps:

(a) providing a library of nucleotide analog-containing subtracter DNA which is susceptible to the digestion of a nucleotide analog-removing enzyme;

(b) contacting the denatured nucleotide analog-containing subtracter DNA with a library of denatured tester DNA which is not affected by the nucleotide analog-removing enzyme, to form a denatured mixture;

(c) permitting both nucleotide analog-containing subtracter DNA and tester DNA in the denatured mixture under conditions sufficient to form double-stranded hybrid duplexes comprise of homo- and hetero-duplexes;

(d) digesting the nucleotide analog-containing hybrid DNA with the nucleotide analog-removing enzyme to generate abasic-nicks/gaps in the subtracter homoduplex and the subtracter-tester heteroduplex; and (e) breaking the abasic-nicks/gaps with a single-strand-specific nuclease and thereby provide a library enriched in the library of tester DNA but almost absent in the library of subtracter DNA.

The preferred embodiment of the present invention method additionally may include the pre-steps of forming double-stranded amplicon DNA of the sample, and prior to commencing the aforementioned step (a):

(1) restricting the initial DNA library with a restriction-endonuclease to generate 5'-cohesive termini on both ends;

(2) ligating a specific adaptor to the ends of the restricted DNA where a template is generated for binding with a specific complementary-primer; and (3) incubating the ligated DNA in denatured form with the specific primer under conditions sufficient to permit the template-dependent extension of the primer to thereby enrich the amount of the initial DNA library and also provide an opportunity for incorporating nucleotide analog into the subtracter in the step (a).

In one aspect of the preferred embodiment described above, steps (b)–(e) are repeated on the enriched library at least once. Advantageously, the enriched library can be made from either a cDNA library or a genomic DNA library. In another aspect of this preferred embodiment, the enriched library is amplified, preferably, by PCR in the pre-step (3).

To increase subtraction force, the subtracter is preferably generated by incorporation with uridine-nucleotide analog (dU) to raise the bonding efficiency by forming adenine-uracil bonding (as in RNA) which is more stable than traditional adenine-thymine bonding (as in DNA). Most preferably, the uridine analog is deoxyuridine triphosphate. Advantageously, the nucleotide analog-containing subtracter DNA is susceptible to the digestion of a nucleotide analog-removing enzyme which can remove entire nucleotide analog or its base structure from the nucleotide analog-containing DNA, while the tester DNA is not affected. Preferably, the nucleotide analog-removing enzyme is a uracil-removing enzyme; most preferably, the uracil-DNA glycosylase (UDG).

According to another aspect of this embodiment, the nucleotide analog is incorporated into the subtracter DNA by DNA polymerase. Preferably, the DNA polymerase is Taq polymerase. To prevent the reassociation of undesired tester-sequences during sequentially enzymatic digestion, the nucleotide analog-removing enzyme only generates partial single-stranded duplexes by introducing abasic-nicks/gaps within the tester-subtracter hybrid duplexes after removing the incorporated nucleotide analog or its base structure. Advantageously, the partial single-stranded duplexes are susceptible to the digestion of single-strand-specific nuclease. Preferably, the nuclease is the nuclease S1 or Mung-Bean nuclease. Preferably, the tester DNA and nucleotide analog-containing subtracter DNA have a ratio of between about 1:10 and about 1:150; most preferably, the ratio is 1:50.

The present invention is also a kit for performing subtractive hybridization of cDNA or genomic DNA libraries, comprising individual ones, or any combinations thereof, of the following components:

(a') deoxyuridine triphosphate which confers susceptibility to the digestion of uracil-removing enzyme upon incorporation into a DNA molecule;

(b') a specific tester-adaptor/primer which protects both ends of the tester from the digestion of single-strand-specific nuclease, and also confers amplification-capability to the tester DNA;

(c') a specific subtracter-adaptor/primer which is unprotected from the digestion of uracil-removing enzyme, and confers amplification-capability to the uracil-containing subtracter DNA;

(d') a template-dependent dU-incorporation activity;

(e') a uracil-removing enzyme;

(f') a uracil-removing enzyme buffer;

(g') a single-strand-specific nuclease; and (h') a nuclease buffer.

Preferably, the specific adaptors/primers for tester and subtracter are those shown in Table 1, which is a list of preferred adaptors/primers used in the preferred embodiment of the present invention, and the dU-incorporation activity in (d') is rendered by Taq polymerase. Advantageously, the uracil-removing enzyme is uracil-DNA glycosylase and the single-strand-specific nuclease is nuclease S1.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIGS. 1a–1b is a flowchart of a preferred embodiment of the nucleotide analog-containing hybrid subtraction of the subject invention;

FIGS. 3a–3b is an illustration of second preferred embodiment of the nucleotide analog-containing hybrid subtraction of the subject invention;

FIGS. 4a–4b is an illustration of third preferred embodiment of the nucleotide analog-containing hybrid subtraction of the subject invention;

FIGS. 5a–5b is a detailed illustration of the sequentially enzymatic digestion from step 3 to step 6 of FIG. 2;

FIG. 7 is a table listing the specific adaptors/primers for tester and subtracter utilized in the present invention.

DESCRIPTION OF THE PREFERRED EMBODIMENT

Figure 1A:
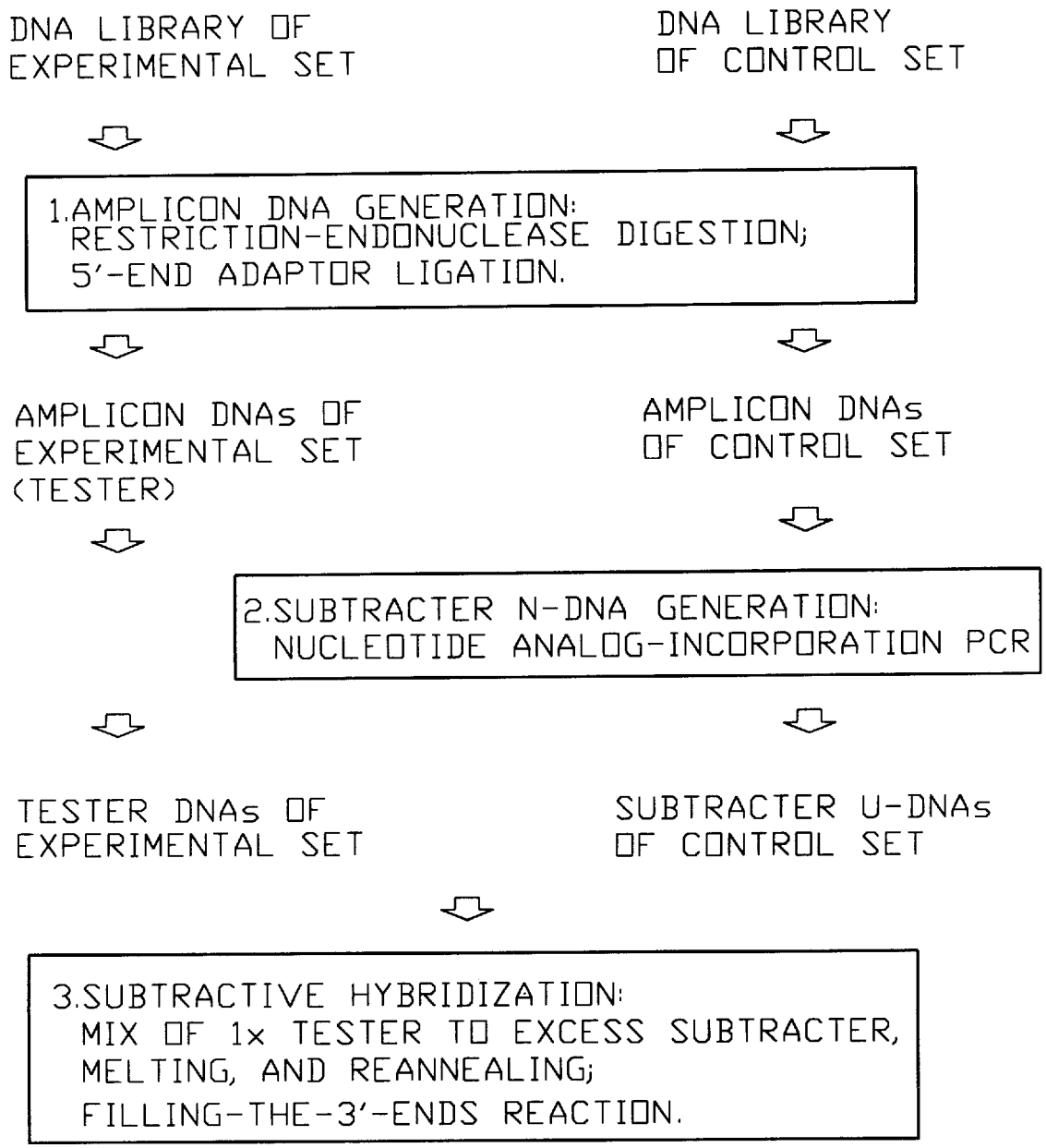

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is directed to an improved subtractive hybridization method, called nucleotide analog-containing DNA subtraction assay (NDSA), for screening different sequences between two cDNA or genomic DNA libraries. This method is primarily designed for quickly isolating different expression genes (either up- or down-regulated), easily detecting large genomic deletions/insertions, and precisely searching chromosome-specific loci. The preferred version of the present invention is based on: the nucleotide analog-incorporated subtracter hybridization with non-modified tester DNA, the abasic-nick/gap generation in common sequences by a nucleotide analog-removing enzyme, and the abasic-nick/gap cleavage by a single-strand-specific nuclease. In conjunction with an adaptor-ligation and a specific PCR amplification, a very small amount of DNA library can be used as an initial sample for this method.

As used herein, tester DNA refers to the DNA isolated from treated, mutated, infected, differentiated, or abnormal cell source, while subtracter DNA refers to the DNA isolated from a cell source with different status, such as non-treated, un-/further-differentiated, and relatively normal cells (or tissue with nearly homogeneous cells). And, such referring can be done vice versa. The tester DNA library contains desired sequences which are abundant in the tester but very limited in the subtracter. The desired sequences represent the differences of gene expression (if a cDNA library is used), or those of genomic complexity (if a genomic DNA library is used). The isolation of the desired sequences is achieved herein by using a nucleotide analog-incorporated subtracter DNA (subtracter N-DNA) to remove common sequences through hybridization and sequentially enzymatic digestion, which is referred to the digestion of nucleotide analog-removing enzyme and single-strand-specific nuclease. The nucleotide analog-removing enzyme refers to the enzyme which can generate nicks or gaps by removing nucleotide analog or its base structure from double-stranded DNA. The common sequence refers to the sequence which is common to both tester- and subtracter-DNA populations.

The advantages of using nucleotide analog-containing subtracter DNA are as follows: First, during subtractive hybridization, the affinity of subtracter to homologous tester can be greatly enhanced by the nucleotide analog-incorporation, such as dU-incorporation which renders a RNA-like character to the subtracter to increase the stability of bonding with tester DNA (Lehninger et. al., *"Principles of Biochemistry, 2nd Edition "*, pp342–343). This stronger bonding between subtracter and tester accomplishes the completion of homology subtraction. Second, the digestion of nucleotide analog-removing enzyme eliminates all undesired nucleotide analog-containing DNA structure, resulting in a very low background from non-specific subtracter contamination. Third, because the digestion of nucleotide analog-removing enzyme only removes nucleotide analog or its base structure from the subtracter-part of hybrids, this partially-digested subtracter maintains the tester-subtracter hybrids in a partial single-stranded conformation which contains nicks and gaps for digestion by a single-strand-specific nuclease.

Figure 4B:
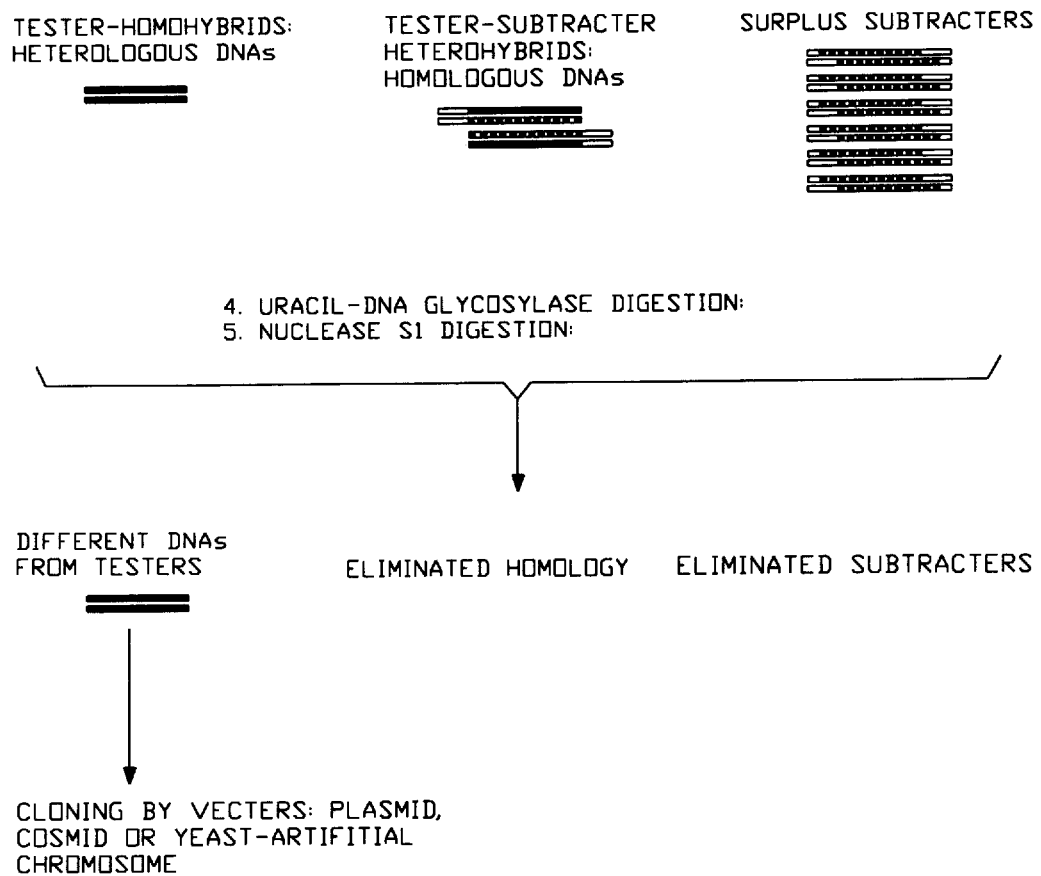
Figure 6A:
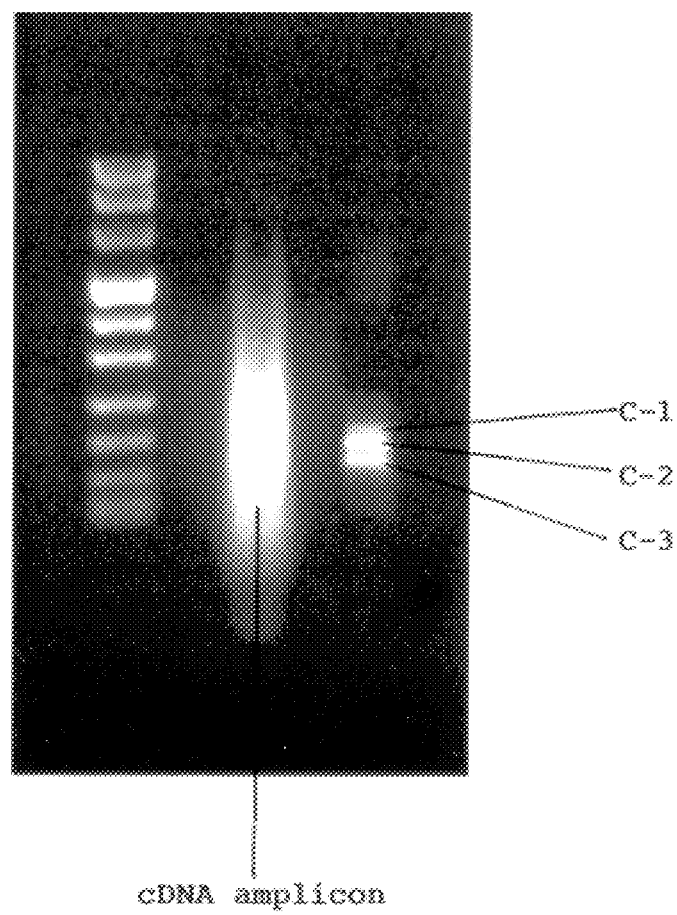
FIGS. 6A–6D are the results of example 4, 6 and 7 of the subject invention.
Figure 6B:
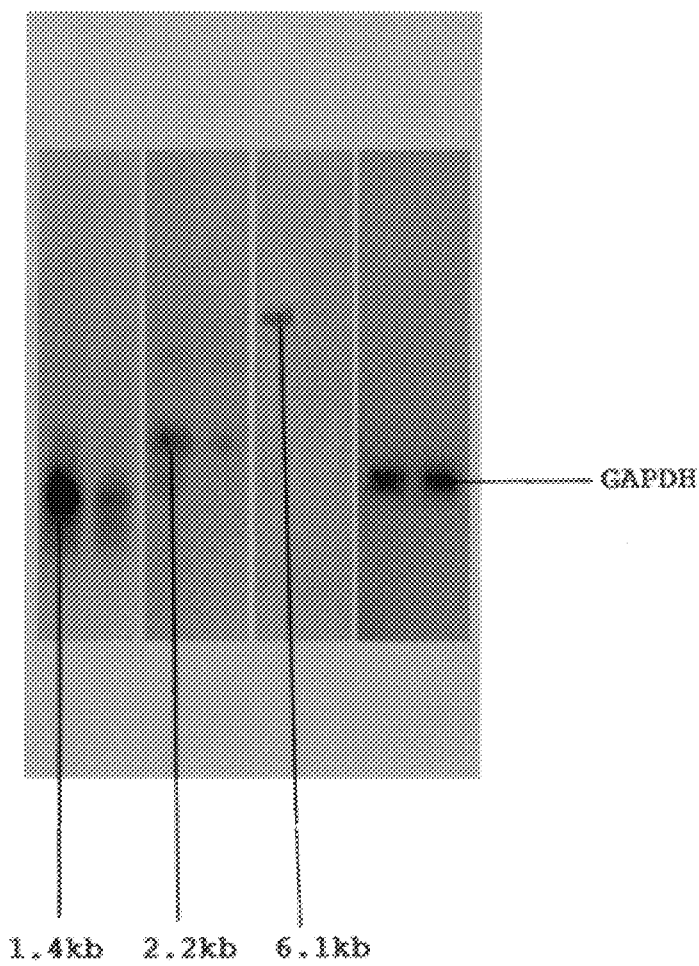
Figure 6C:
Figure 6D:
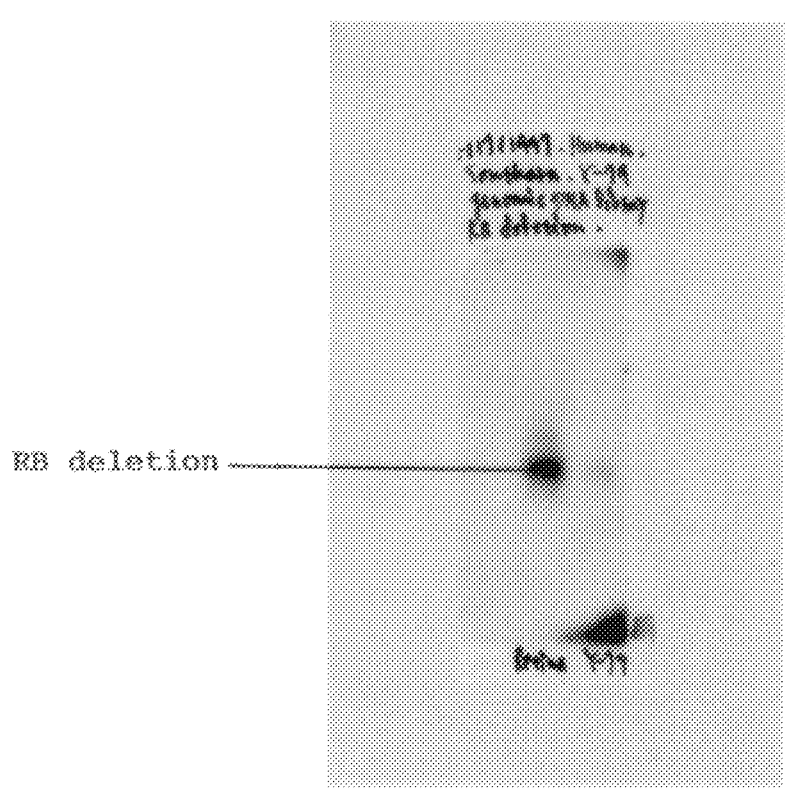

For nucleotide analog-incorporation, the control DNA was digested by a restriction-endonuclease on both ends, preferably a 4-cutter restriction enzyme, and ligated to a specific adaptor. This ligated DNA called subtracter-amplicon is then used to generate nucleotide analog-containing subtracter DNA by a template-dependent primer-extension reaction in the presence of nucleotide analog, preferably by a uracil-incorporation PCR as in the step 2 of FIGS. 3 and 4. Although the specially designed adaptors/primers were used to generate subtracter DNA, any oligonucleotide capable of being extended into nucleotide analog-containing subtracter DNA for the purpose of enzymatic subtraction is within the scope of the present invention. The enzymatic subtraction refers to the elimination of common sequences by the sequentially enzymatic digestion in a subtractive hybridization assay. After nucleotide analog-incorporation, the adaptor part of a subtracter DNA can be either removed by a restriction-enzyme (if the same adaptor is used to generate tester-amplicon) or kept on both ends (if adaptors are different from each other as shown in FIG. 3). Thus, when the starting material is very limited, tester DNA will need to be amplified by a similar procedure as for the subtracter but without the nucleotide analog-incorporation. In another case (as shown in FIG. 4), when the starting material is abundant, tester DNA only needs to be digested by the same restriction-enzyme as does subtracter-amplicon but without the ligation; and after a subtractive hybridization which contains a filling-the-ends reaction before the enzymatic digestion, the blunt-ended desired sequences can escape the digestion and be amplified by a cloning procedure.

In the step 3 of FIGS. 1–5, tester DNA is then mixed with an excess amount of nucleotide analog (preferably dU)-incorporated subtracter, denatured, and hybridized at cooler temperature, preferably 60°–75° C., most preferably 65°–68° C. (Lehninger, et al., *"Principles of Biochemistry, 2nd Edition "*,p343; Sambrook et. al., *"Molecular Cloning, 2nd Edition "*, p10.45). It is preferred that the ratio of subtracter to tester DNA is in the range of about 10:1 to about 150:1. In the most preferred embodiment, the ratio is between 30:1 to 60:1. If the ratio of subtracter to tester is too high, successful enrichment of sequences that are only up- or down-regulated/changed by several fold will not be obtained. If the ratio of subtracter to tester is too low, common sequences will not be completely selected out, and then cause false-positive results which need to be removed by more rounds of subtraction. The optimal ratio of subtracter to tester DNA for isolating a particular sequence will vary depending on the amount of difference between tester and subtracter.

During the hybridization step, three kinds of hybrid duplexes are formed as follows: First, the tester-homohybrid duplexes which consist of heterologous (different) sequences only present in tester but almost absent in subtracter; Second, the tester-subtracter-heterohybrid duplexes which consist of homologous (common) sequences present in both tester and subtracter; And third, the subtracter-homohybrid duplexes which consist of surplus subtracter. Only the ones lacking any nucleotide analog-containing DNA structure will be spared from the sequential digestion of nucleotide analog-removing enzyme and single-strand-specific nuclease; therefore, the tester-homohybrid duplexes can be preserved intact throughout the sequentially enzymatic digestion, whereas the subtracter-subtracter and tester-subtracter duplexes are digested into very small fragments which can not be amplified or cloned. For example, as shown in FIGS. 3 and 4, the UDG cleaves the uracil-bases from uracil-containing hybrid DNAs, resulting in many abasic-nicks and -gaps generated within the subtracter-subtracter and subtracter-tester duplexes (step 4). The nuclease S1 then digests all nicks and gaps to make these abasic sequences into undetected and unamplifiable pieces (step 5). Although the UDG and nuclease S1 were used in a preferred version of the present invention, any enzyme or enzyme-combination capable of digesting subtracter and common sequences in the same matter is within the scope of the present invention. Such contemplated nucleotide analog-removing enzymes and single-strand-specific nucleases for use in the step 4 and 5 include uracil-N-glycosidase (UNG), AP endonuclease and Mung-Bean nuclease (MBN).

Figure 2A:
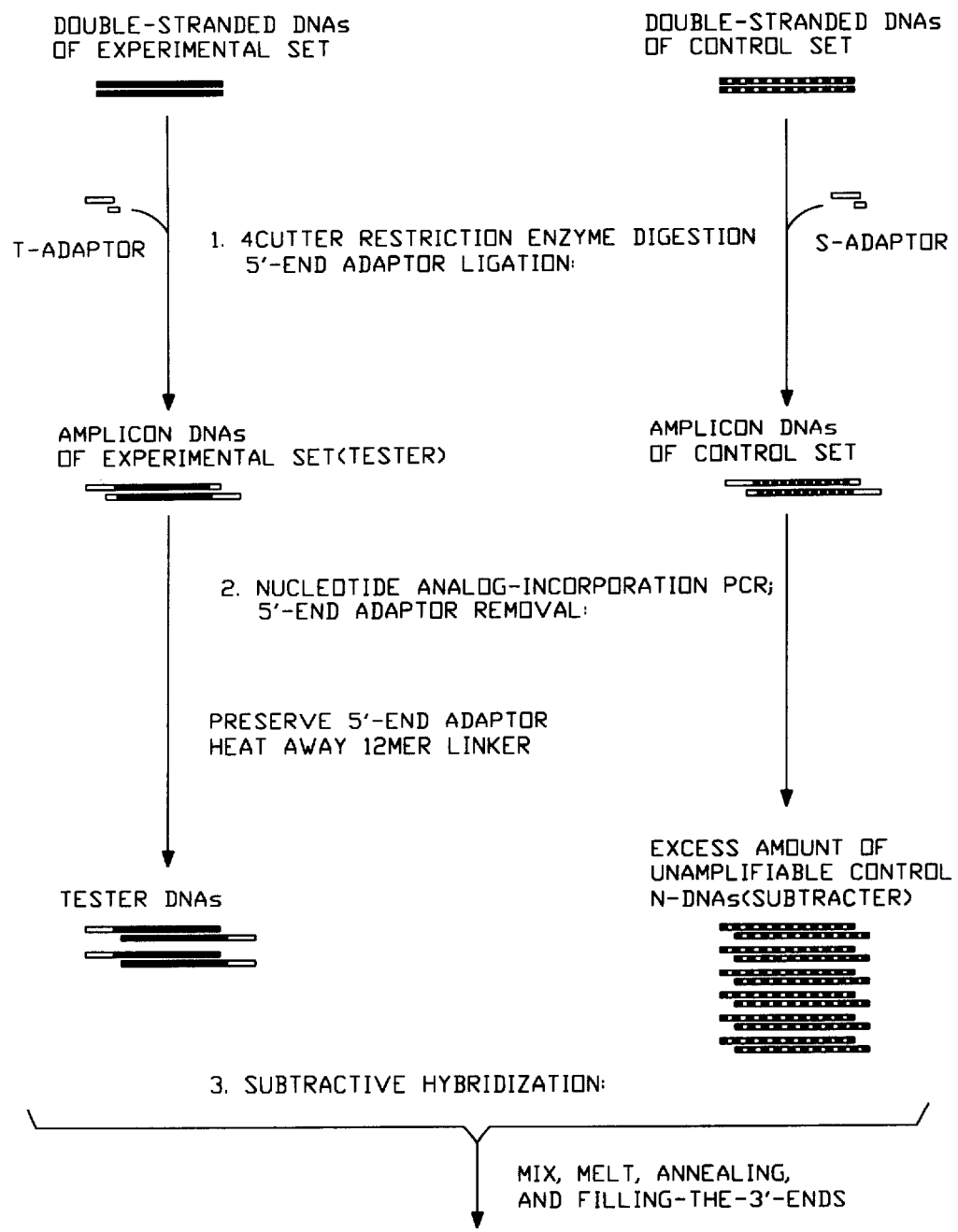
FIGS. 2a–2b is an illustration of the nucleotide analog-containing hybrid subtraction of FIG. 1.
Figure 2B:
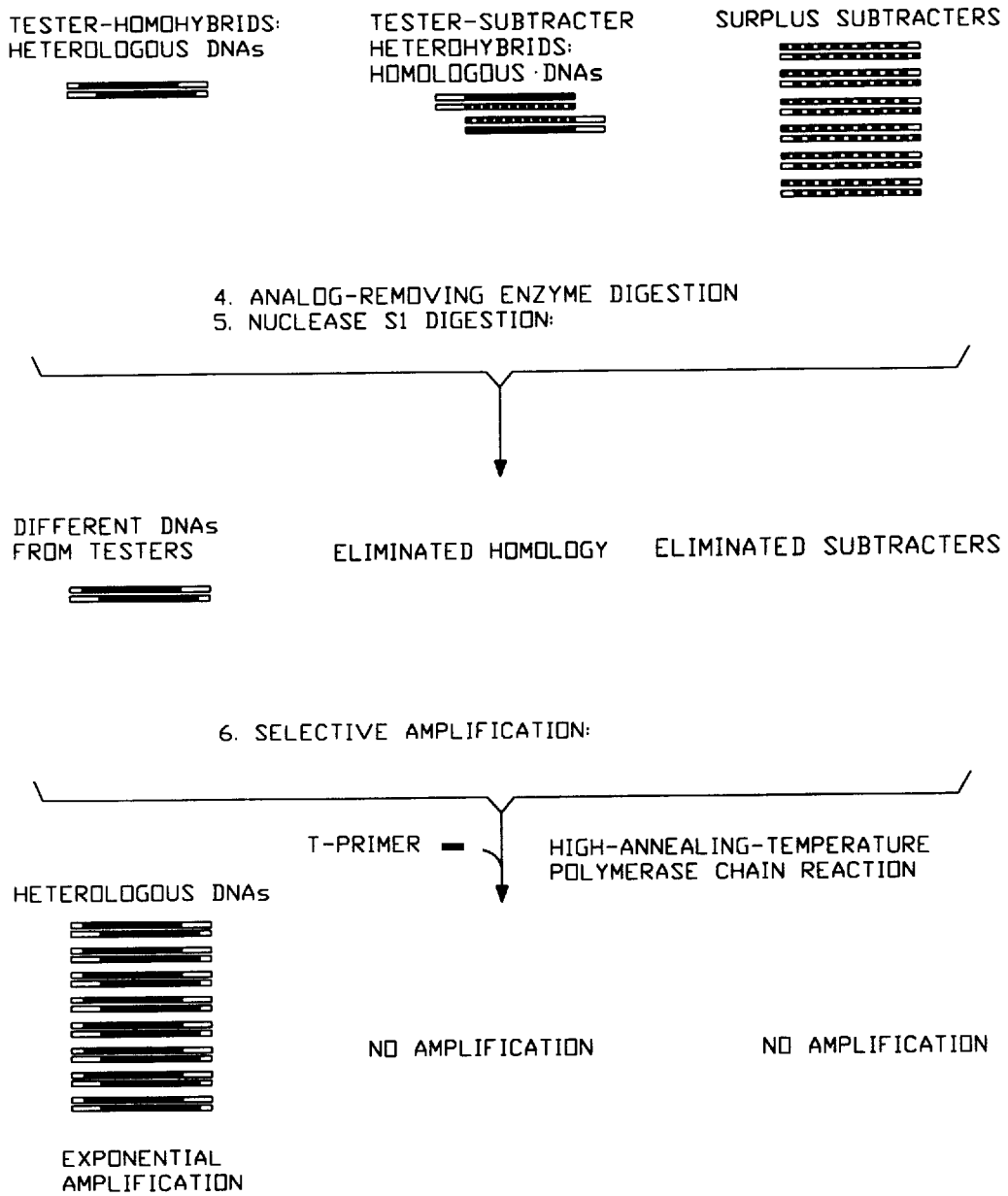

In a preferred embodiment, referring to FIG. 2, when the adaptor of subtracter is removed after nucleotide analog (preferably dU)-incorporation, the tester-homohybrid duplexes will contain adaptor on both ends, whereas the tester-subtracter-heterohybrid duplexes have 5'-adaptor on only one end (step3 in FIG. 2). This results in an exponential amplification of the tester-homohybrid duplexes and a linear amplification of the tester-subtracter-heterohybrid duplexes during an optional selective amplification (step 6 in FIGS. 1 and 2), which can be completed before or after the sequentially enzymatic digestion to emphasize the differences. In this preferred embodiment, selective amplification is accomplished after the sequentially enzymatic digestion for completely preventing any amplification of the tester-subtracter duplexes.

Alternatively as shown in FIG. 3, when the tester-adaptor is different from the subtracter-adaptor, subtractive hybridization can be performed directly without removing the subtracter-adaptor since a mismatched adaptor on both ends will form a single-stranded region (step3 in FIG. 3). In this case, the sequentially enzymatic digestion must be completed before selective amplification for cleaving the mismatched adaptor from the tester-subtracter duplexes, resulting in no amplification during selective PCR. However, since the sequentially enzymatic digestion destroys all contaminating nucleotide analog-containing duplexes, this procedure ensures that only the tester-homohybrid duplex can be isolated at final. Thus, the removing of adaptor confers additional subtraction force for reducing the potential contamination from tester-subtracter or subtracter-subtracter duplexes.

The subtracted tester DNA can be subjected to another round of subtraction or amplified by PCR. The final subtracted or selectively amplified sequences are used for DNA library selection assay and clonal analysis, and represent the desired different DNAs which are stimulated or up-regulated in the treated, mutated, infected, differentiated, or abnormal cells. By the same token, the tester and subtracter steps can be done in reverse order to isolate the suppressed or down-regulated DNAs. The final isolated sequence can then be used to probe the full-length mRNA or cDNA from the tester library (if cDNA tester is used), or to locate the deleted/inserted loci in a special chromosome by in-situ-hybridization (if genomic DNA is used). The information so obtained will provide further understanding of a variety of diseases, physiological phenomena, and genetic functions.

The present invention will be very useful in the identification of different gene expression involved in development, cell differentiation, aging, and variety of pathological disorders, such as cancer formation, genetic defects, autoimmune diseases, and any other disorders related to genetic malfunction. The identification of these differentially expressed genes will help the determination of their open-reading frames and corresponding peptides which may contribute to a specific drug-design or therapy for regulation of theses genes. Such therapeutic approaches include transcription inhibitors, monoclonal antibodies, antisense RNA, and chemicals that can interact with the gene or its protein product to cure or alleviate related disorders. For example, the methods of the present invention can be used to screen candidate genes for gene therapy to correct inherent defects. When a defect is caused by stimulation of a specific unknown gene, the identification of this gene will help the design of antisense ogilonucleotides against the gene or production of monoclonal antibodies against the corresponding protein product.

Alternatively, the present invention can also be used to screen some types of chromosomal abnormalities, such as deletion and insertion. Because genomic DNA fragments of less than one kilobase are prepared by restriction-enzyme digestion before subtractive hybridization (Lisitsyn et. al., Science 259: 946–951(1993)), the target deletion or insertion must be larger than this size for efficient amplification. The identification of these chromosomal deletions or insertions may contribute to the diagnosis or prognosis of certain virus infections, inherent problems, or developmental defects. For example, p16 deletion is very well known to happen in familial melanoma. If the deletion can be identified as early as possible, this information may help potential patients to prevent the onset of melanoma.

Although nucleotide analog-containing DNA subtraction assay (NDSA) is primarily designed for medical and biological research, the method will also be useful to pharmaceutical, agricultural, and environmental research which involves biological systems. For example, when the gene expression is compared between drug-treated and non-treated cells, the results may indicate the mechanism by which this drug acts. For another example, when the genomic DNAs from disease-resistant plant cells are compared with those from disease-susceptible plant cells, the results will be the candidate loci for the resistant gene(s). Taken together, the NDSA is capable of providing variety of information for understanding the changes of gene expression and the differences between genomes.

In the preferred embodiments (as shown in FIGS. 3 and 4) of the present invention, according to the high activity of UDG- and nuclease S1-digestion, the labor- and time-consuming factors in this subtractive hybridization assay can be reduced to the minimum. Also, the preparation for uracil-containing subtracter DNA is cheaper and more efficient than other "modified nucleotide"- or "nucleotide analog"-incorporation which is widely used in previous methods. Most importantly, such sequentially enzymatic digestion can be carried out continuously at room temperature with the change of buffer only once. Taken together, these special features make NDSA as fast, simple, and inexpensive as a kit for concisely isolating different sequences of interest.

Although certain preferred embodiments of the present invention have been described, the spirit and scope of the invention is by no means restricted to what is described above. For example, within the general framework of (a) one or more specific adaptors/primers for nucleotide analog-incorporation and selective amplification; (b) one or more nucleotide analog-incorporation into subtracter; (c) enzyme or enzyme combination which can remove nucleotide analog or its base structure from subtracter-tester hybrid duplexes; (d) enzyme or enzyme combination which has the capability of single-strand-specific digestion for the elimination of nicked/gapped subtracter-subtracter and subtracter-tester hybrid duplexes, there is a very large number of permutations and combinations possible, all of which are within the scope of the present invention. For example, even though only UDG and nuclease S1 are shown in each of drawings, the possible substitutes could be UNG, AP endonuclease and MBN, or else that has the same functional activity.

EXAMPLE 1 cDNA Library Preparation

LNCaP cells, a prostate cancer cell line, were grown in DMEM medium supplemented with 2% fetal calf serum (FBS). For three-day activin treatment, 6 dishes of control cells were treated with 1.5 ml 200 ng/ml activin per day, while 4 dishes of experimental cells were activin treated with 1.5 ml 2% FBS per day. On the fifth day after the first treatment, 60% reduction in growth was observed in the activin treated cells compared to the experimental cells by microscopy and cell counting. The cells were trypsinized and total RNAs were isolated with TRIzol reagent (GIBCO/BRL). mRNAs were purified from total RNAs with a poly (oligo-dT) dextran column (Oligotex Direct Mini kit, Qiagen). 4 $\mu$g mRNAs were mixed with an oligo-dT primer and heated to 65° C. (10 min). Reverse transcription (RT) was performed with an oligo-dT primer following the manufacturer's protocol of cDNA Cycle kit in the Invitrogen, and the products were phenol-extracted, isopropanol-precipitated and resuspended in 40 $\mu$l 10 mM Tris-buffer. All RT products (2~3 $\mu$g) were used to synthesize second strand cDNAs (ds-cDNAs) with a DNA polymerase1-$T_4$ ligase-RNase H mixture (Ueli et. al.,*Gene,* 25: pp263–269 (1983)). 500 ng of experimental double-stranded cDNAs were digested by a four-cutting enzyme, such as 5 U/$\mu$l Hpa2 (4 h, 37° C.), and prepared for 5'-end ligation in a pre-reaction volume of 47 $\mu$l containing: 1 $\mu$l 4 $\mu$g/$\mu$l T-hpa-24mer oligo, 1 $\mu$l 2 $\mu$g/$\mu$l dephosphorylated T-hpa-12mer oligo, 5 $\mu$l ligase buffer and ddH$_2$O. Before 3 $\mu$l 5 U/$\mu$l $T_4$ ligase was added, the 47 $\mu$l mixture was heated to 50° C. (2 min), and gradually cooled down to 10° C. over a period of one hour, and then the ligation was performed at 14° C. (16 h). This formed the tester-amplicon. For subtracter-amplicon generation, 500 ng Hpa2-restricted control cDNAs were ligated to the S-hpa-12/24mer adaptors in the manner described above.

Uridine analogs were incorporated into the subtracter sequence as described below.

EXAMPLE 2

Uridine Analog-incorporation

The subtracter-amplicon was diluted to 10 µg/ml, and four PCR reactions were set up on ice to generate subtracter U-DNA for the control set. Each 50 µl reaction contained 2 µl diluted ligation, 1 µl 4 µg/µl S-hpa-24mer oligo, 2 µl dNTPs (10 mM dATP, 10 mM dCTP, 10 mM dGTP, and 30 mM dUTP), 5 µl 10×PCR buffer, 1 µl 3.5 U/µl Taq DNA polymerase and ddH$_2$O. The S-hpa-12mer was melted away (5 min, 72° C.), and ends filled in with Taq DNA polymerase (7 min, 72° C.). Twenty-one cycles of amplification were performed (1 min, 95° C.; 3 min, 72° C.), and the products were phenol-extracted, isopropanol-precipitated and resuspended in 20 µl 10 mM Tris-buffer each (Sambrook et.al., "Molecular Cloning, 2nd Edition ", p10.49 (1989)). The S-adaptors were then removed with Hpa2-restriction, and the restricted products (subtracters) were phenol-extracted, isopropanol-precipitated, combined and resuspended in a total 16 µl EE×3 buffer (30 mM EPPS, pH 8.0 at 20° C.; 3 mM EDTA). 6 µl (9 µg) subtracters were measured on a 2.5% TBE-agarose gel.

The tester cDNA fragments were hybridized with subtracter U-DNA fragments as described in the following example.

EXAMPLE 3
Subtractive Hybridization and Selective Amplification

For subtractive hybridization, 300 ng of T-adaptor-ligated tester-amplicon (testers) from non-treated cells was dissolved by 10 µl subtracter-containing solution and denatured at 98° C. (6 min). The mixture was then cooled on ice (2 min), added with 2 µl 5M NaCl to adjust salt concentration, vortexed, overlaid mineral oil, and incubated at 67° C. (20 h). The hybridized-DNAs were diluted with 20 µl MgCl$_2$ solution (2.5 mM) and two 50 µl PCR reactions were set up with 2 µl diluted hybrids, 1 µl 4 µg/µl T-hpa-24mer oligo, 2 µl dNTPs (10 mM dATP, 10 mM dCTP, 10 mM dGTP, and 10 mM dTTP), 5 µl 10×PCR buffer, 1 µl Taq/Pwo DNA polymerase mixture (3.5 U/µl) and 39 µl ddH$_2$O. The T-hpa-12mer was melted away (5 min, 72° C.), and ends filled in with Taq/Pwo DNA polymerase (7 min, 72° C.). Six-cycles of amplification were performed (1 min, 95° C.; 3 min, 70° C.), and the products were phenol-extracted, isopropanol-precipitated and resuspended in 17 µl 1×PCR buffer.

Enzymatic digestion of hybridized DNA was accomplished as described below.

EXAMPLE 4
Sequentially Enzymatic Digestion

5 µl uracil-DNA glycosylase (1 U/µl) was added (2 h, 20° C.) to above products to remove uracil-bases, resulting in generating abasic-nicks/gaps in the tester-subtracter hybrids and surplus subtracters. These abasic-sites were then susceptible to the nick/gap-digestion of 1 µl 2 U/µl nuclease S1 (30 min, 25° C.), and then the digest was phenol-extracted, isopropanol-precipitated and resuspended in 20 µl 10 mM Tris-buffer. Final selective amplification were set up on ice, containing: 2 µl digest, 1 µl 4 µg/µl T-hpa-24mer oligo and same as aforesaid. The procedure was as described above, with the differences that 1 µl Taq/Pwo DNA polymerase mixture was added at 80° C. and a twenty-cycle PCR was performed. Final products were combined, phenol-extracted, isopropanol-precipitated and resuspended with 20 µl 10 mM Tris-buffer to give the desired different sequences. Recovery of the final product was accomplished by Gel Extraction (Qiagen kit) from electrophoresis on 2.5% agarose gel (FIG. 6-A).

The subtracted library was constructed as described below.

EXAMPLE 5
Cloning and Sequencing of Difference Products

Final difference products were cloned into the blunt site of a pCD21 vector using a Clontech TA Cloning kit. The double-stranded vector was amplified in INVαF' cells (Invitrogen), prepared using a miniprep column (Qiagen), and sequenced with Sequenase v.2 DNA sequencing kit (Amersham) by dideoxy-mediated chain termination. Resulting sequences were searched and compared to the Genbank database using the BLAST program.

The successful isolation of differentially expressed genes was confirmed by Northern blot hybridization as described below.

EXAMPLE 6
Northern Blot Hybridization

Total RNA (8 µg) isolated from both non-treated and activin-treated LNCap cells was separated by electrophoresis through 0.9% agarose-formaldehyde gel and transferred to nylon filter (Schleicher & Schuell). The filter was dried and baked under UV-light (30 sec.) DNA probes from three PCR-amplified inserts (probe C-1, C-2, and C-3 in FIG. 6-A) were prepared with a Prime-It random labeling kit (Strategene) in the presence α-[$^{32}$P] dATP. Northern blot hybridization was carried out for 4 hours at 68° C. in QuikHyb solution (Strategene). Blots were washed with 2% SSC, 0.1% SDS solution at room temperature twice (15 min each), followed by a 1 hour wash in 0,1% SSC, 0.1% SDS solution at 65° C.

As shown in FIG. 6-B, three specific mRNAs of approximately 1.4, 2.2 and 6.1 kilobase were detected in the non-treated cells but much less in the activin-treated cells by C-2, C-3, and C-1, respectively. The sequencing result of the 6.1 kilobase mRNA confirmed a down-regulation of Bcl-2 gene expression which is highly related to growth reduction of activin-treated LNCaP cells.

EXAMPLE 7
Detection of Genomic Deletion in Retinoblastoma Cells

Y-79, a retinoblastoma cell, has been known to contain an RB-deletion in its genome. As a model of genomic subtraction by USA, the genomic DNAs of normal retina cells and Y-79 cells were isolated by the IsoQuick nucleic acid extraction kit (Microprobe), restricted with Hpa2, and ligated to T-hpa-adaptor and S-hpa-adaptor respectively to give the tester (normal cell) and subtracter (Y-79). The size of restricted genomic DNA was about 1 kilobase which can be efficiently amplified by PCR. The uridine analog was incorporated into subtracter as described in Example 2. The subtractive hybridization method described in Example 3. was accomplished following by sequentially enzymatic digestion described in Example 4. The resulting subtracted tester DNA (FIG. 6-C) was amplified by PCR, cloned into a prokaryotic expression vector, and used to transform competent cells. These cloned DNA fragments were then purified, random-prime labeled, and used to probe a Southern blot of genomic DNA fragments isolated from tester and subtracter. A signal was detected on the normal DNA but not Y-79 DNA (FIG. 6-D). The sequencing result of this signal indicated a 108 base deletion in RB-exon 1.

Defined in detail, the present invention is a method of performing subtractive hybridization, comprising the steps of: (a) providing a first library of nucleotide analog-containing subtracter DNA, wherein said nucleotide analog-containing subtracter DNA is susceptible to digestion by a nucleotide analog-removing enzyme; (b) contacting said nucleotide analog-containing subtracter DNA in denatured form with a second library of denatured tester DNA, wherein said tester DNA is protected from digestion by said nucleotide analog-removing enzyme, to form a denatured mixture; (c) permitting said nucleotide analog-containing subtracter DNA and tester DNA in said denatured mixture to form double-stranded hybrid DNA comprising homo- and hetero-duplexes; (d) digesting susceptible hybrid DNA with said nucleotide analog-removing enzyme; and (e) treating the resulting material with a single-strand-specific nuclease to digest abasic-nick/gap-containing duplexes and thereby provide a library enriched in tester DNA that is not present in said library of subtracter DNA; (f) whereby said method provides a fast, simple and reliable isolation of desired different sequences from said two DNA libraries.

Alternatively defined in detail, the present invention is a kit for performing improved subtractive hybridization, comprising: (a) a specific tester-adaptor/primer, wherein said tester-adaptor/primer protects both ends of the tester from digestion by nucleotide analog-removing enzyme and single-strand-specific nuclease, and also confers amplification-capability to the tester DNA; (b) a specific subtracter-adaptor/primer; wherein said subtracter-adaptor/primer is susceptible to digestion by nucleotide analog-removing enzyme or single-strand-specific nuclease, and confers amplification-capability to the subtracter; (c) deoxynucleotide triphosphate analogs; wherein said analogs confer susceptibility to nucleotide analog-removing enzyme digestion upon incorporation into a DNA molecule; (d) a template-dependent nucleotide analog-incorporation activity; (e) a nucleotide analog-removing enzyme; (f) a nucleotide analog-removing enzyme buffer; (g) a single-strand-specific nuclease; and (h) a nuclease buffer; (i) whereby said said can be used to provide a fast, simple and reliable isolation of desired different sequences from said two DNA libraries.

Defined broadly, the present invention is a method of performing subtractive hybridization, comprising the steps of: (a) providing a first library of subtracter DNA, wherein said DNA is susceptible to digestion by a nicking-/gapping-enzyme; (b) contacting said subtracter DNA in denatured form with a second library of denatured tester DNA, wherein said tester DNA is protected from digestion by said nicking-/gapping-enzyme, to form a denatured mixture; (c) permitting said subtracter DNA and tester DNA in said denatured mixture to form double-stranded hybrid DNA comprising homo- and hetero-duplexes; (d) digesting susceptible hybrid DNA with said nicking-/gapping-enzyme; and (e) treating the resulting material to digest abasic-nick/gap-containing duplexes and thereby provide a library enriched in tester DNA that is not present in said library of subtracter DNA; (f) whereby said method provides a fast, simple and reliable isolation of desired different sequences from said two DNA libraries.

Alternatively defined broadly, the present invention is a kit for performing improved subtractive hybridization, comprising: (a) a specific tester-adaptor/primer, wherein said tester-adaptor/primer protects both ends of the tester from digestion by a nicking-/gapping-enzyme and nuclease, and also confers amplification-capability to the tester DNA; (b) a specific subtracter-adaptor/primer, wherein said subtracter-adaptor/primer is susceptible to digestion by said nicking-/gapping-enzyme or nuclease, and confers amplification-capability to the subtracter; (c) deoxynucleotide triphosphate analogs, wherein said analogs confer susceptibility to said nicking-/gapping-enzyme digestion; (d) a template-dependent extension activity; (e) an enzyme; and (f) a nuclease; (g) whereby said kit can be used to provide a fast, simple and reliable isolation of desired different sequences from said two DNA libraries.

Defined more broadly, the present invention is a method of performing subtractive hybridization, comprising the steps of: (a) providing a first library of subtracter DNA which is susceptible to digestion by an enzyme; (b) providing a second library of tester DNA which is protected from digestion by said enzyme; (c) contacting said first library of subtracter DNA and said second library of tester DNA to obtain a mixture containing double-stranded hybrid DNA which include susceptible hybrid DNAs; (d) treating said mixture with said enzyme to digest said susceptible hybrid DNAs, to obtain a treated mixture containing nicked-and-gapped hybrid DNAs; and (e) further treating said treated mixture to digest said nicked-and-gapped hybrid DNAs, to obtain a resultant mixture containing digestion-resistant hybrid DNAs which is enriched in tester DNA that is not present in said library of subtracter DNA; (f) whereby said method provides a fast, simple and reliable isolation of desired different sequences from said two DNA libraries.

Alternatively defined more broadly, the present invention is a kit for performing improved subtractive hybridization, comprising: (a) a subtracter DNA library which susceptible to digestion by an enzyme; (b) a tester DNA library which is protected from digestion by said enzyme; (c) said enzyme which can nick or gap said susceptible DNA; and (d) a treatment material which can digest nicked-and-gapped hybrid DNAs; (e) whereby said kit can be used to provide a fast, simple and reliable isolation of desired different sequences from said two DNA libraries.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A method of performing subtractive hybridization, comprising the steps of:
    a. providing a first library of nucleotide analog-containing subtracter DNA, wherein said nucleotide analog-containing subtracter DNA is susceptible to digestion by a nucleotide analog-removing enzyme;
    b. contacting said nucleotide analog-containing subtracter DNA in denatured form with a second library of denatured tester DNA, wherein said tester DNA is protected from digestion by said nucleotide analog-removing enzyme, to form a denatured mixture;
    c. permitting said nucleotide analog-containing subtracter DNA and tester DNA in said denatured mixture to form double-stranded hybrid DNA comprising homo- and hetero-duplexes;
    d. digesting susceptible hybrid DNA with said nucleotide analog-removing enzyme; and
    e. treating the resulting material with a single-strand-specific nuclease to digest abasic-nick/gap-containing duplexes and thereby provide a library enriched in tester DNA that is not present in said library of subtracter DNA;
    f. whereby said method provides an isolation of desired different sequences from said two DNA libraries.

2. The method as defined in claim 1, further comprising the step of repeating steps (b) through (e) on said enriched library at least one time.

3. The method as defined in claim 1, further comprising the step of amplifying said enriched library.

4. The method as defined in claim 3, wherein said amplification is PCR amplification.

5. The method as defined in claim 1, wherein said subtracter DNA is susceptible to digestion by said nucleotide analog-removing enzyme by incorporating therein nucleotide analogs.

6. The method as defined in claim 5, wherein said nucleotide analogs are deoxyuridine triphosphates.

7. The method as defined in claim 5, wherein said nucleotide analogs are incorporated into said subtracter DNA by DNA polymerase.

8. The method as defined in claim 7, wherein said DNA polymerase is Taq polymerase.

9. The method as defined in claim 1, wherein said homo- and heteroduplexes are formed by the heat-melting and then cool-reannealing technique.

10. The method as defined in claim 1, wherein said nucleotide analog-removing enzyme is uracil-DNA glycosylase.

11. The method as defined in claim 1, wherein said single-strand-specific nuclease is nuclease S1.

12. The method as defined in claim 1, wherein said nucleotide analog-containing subtracter DNA and said tester DNA have a ratio of between about 10:1 and about 150:1.

13. The method as defined in claim 12, wherein said ratio is about 50:1.

14. A kit for performing improved subtractive hybridization, comprising:
   a. a specific tester-adaptor/primer, wherein said tester-adaptor/primer protects both ends of the tester from digestion by single-strand-specific nuclease, and also confers amplification-capability to a tester DNA;
   b. a specific subtracter-adaptor/primer, wherein said subtracter-adaptor/primer is susceptible to digestion by nucleotide analog-removing enzyme or single-strand-specific nuclease, and confers amplification-capability to a subtracter;
   c. deoxynucleotide triphosphate analogs, wherein said analogs confer susceptibility to nucleotide analog-removing enzyme digestion upon incorporation into a DNA molecule;
   d. a template-dependent nucleotide analog-incorporation activity;
   e. a nucleotide analog-removing enzyme;
   f. a nucleotide analog-removing enzyme buffer;
   g. a single-strand-specific nuclease; and
   h. a nuclease buffer;
   i. whereby said kit can be used to provide an isolation of desired different sequences from said two DNA libraries.

15. The kit as defined in claim 14, wherein said analogs are deoxyuridine triphosphate.

16. The kit as defined in claim 14, wherein said template-dependent nucleotide analog-incorporation activity is Taq polymerase.

17. The kit as defined in claim 14, wherein said nucleotide analog-removing enzyme is uracil-DNA glycosylase.

18. The kit as defined in claim 14, wherein said single-strand-specific nuclease is nuclease S1.

19. A method of performing subtractive hybridization, comprising the steps of:
   a. providing a first library of subtracter DNA, wherein said DNA is susceptible to digestion by a nicking-/gapping-enzyme;
   b. contacting said subtracter DNA in denatured form with a second library of denatured tester DNA, wherein said tester DNA is protected from digestion by said nicking-/gapping-enzyme, to form a denatured mixture;
   c. permitting said subtracter DNA and tester DNA in said denatured mixture to form double-stranded hybrid DNA comprising homo- and hetero-duplexes;
   d. digesting susceptible hybrid DNA with said nicking-/gapping-enzyme; and
   e. treating the resulting material to digest abasic-nick/gap-containing duplexes and thereby provide a library enriched in tester DNA that is not present in said library of subtracter DNA;
   f. whereby said method provides an isolation of desired different sequences from said two DNA libraries.

20. The method as defined in claim 19, further comprising the step of repeating steps (b) through (e) on said enriched library at least one time.

21. The method as defined in claim 19, further comprising the step of amplifying said enriched library.

22. The method as defined in claim 21, wherein said amplification is PCR amplification.

23. The method as defined in claim 19, wherein said subtracter DNA is nucleotide analog-containing subtracter DNA.

24. The method as defined in claim 23, wherein said nicking-/gapping-enzyme is nucleotide analog-removing enzyme.

25. The method as defined in claim 24, wherein said subtracter DNA is susceptible to digestion by said nucleotide analog-removing enzyme by incorporating therein nucleotide analogs.

26. The method as defined in claim 25, wherein said nucleotide analogs are deoxyuridine triphosphates.

27. The method as defined in claim 25, wherein said nucleotide analogs are incorporated into said subtracter DNA by DNA polymerase.

28. The method as defined in claim 27, wherein said DNA polymerase is Taq polymerase.

29. The method as defined in claim 19, wherein said homo- and heteroduplexes are formed by the heat-melting and then cool-reannealing technique.

30. The method as defined in claim 24, wherein said nucleotide analog-removing enzyme is uracil-DNA glycosylase.

31. The method as defined in claim 19, wherein in said step (e) the resulting material is treated with a single-strand-specific nuclease.

32. The method as defined in claim 31, wherein said single-strand-specific nuclease is nuclease S1.

33. The method as defined in claim 19, wherein said subtracter DNA and said tester DNA have a ratio of between about 10:1 and about 150:1.

34. The method as defined in claim 33, wherein said ratio is about 50:1.

35. A kit for performing improved subtractive hybridization, comprising:
   a. a specific tester-adaptor/primer, wherein said tester-adaptor/primer protects both ends of the tester from digestion by a nuclease, and also confers amplification-capability to a tester DNA;
   b. a specific subtracter-adaptor/primer, wherein said subtracter-adaptor/primer is susceptible to digestion by a nicking-/gapping- enzyme or said nuclease, and confers amplification-capability to a subtracter;
   c. deoxynucleotide triphosphate analogs, wherein said analogs confer susceptibility to said nicking-/gapping-enzyme digestion;
   d. a template-dependent extension activity;
   e. a nicking-/gapping- enzyme; and
   f. a nuclease;
   g. whereby said kit can be used to provide an isolation of desired different sequences from said two DNA libraries.

36. The kit as defined in claim 35, further comprising an enzyme buffer.

37. The kit as defined in claim 35, further comprising a nuclease buffer.

38. The kit as defined in claim 35, wherein said nicking-/gapping-enzyme is a nucleotide analog-removing enzyme.

39. The kit as defined in claim 35, wherein said nuclease is a single-strand specific nuclease.

40. The kit as defined in claim 35, wherein said analogs are deoxyuridine triphosphate.

41. The kit as defined in claim 35, wherein said template-dependent extension activity is a nucleotide analog-incorporation activity.

42. The kit as defined in claim 41, wherein said template-dependent nucleotide analog-incorporation activity is Taq polymerase.

43. The kit as defined in claim 38, wherein said nucleotide analog-removing enzyme is uracil-DNA glycosylase.

44. The kit as defined in claim 39, wherein said single-strand-specific nuclease is nuclease S1.

45. A method of performing subtractive hybridization, comprising the steps of:
 a. providing a first library of subtracter DNA which is susceptible to digestion by an enzyme;
 b. providing a second library of tester DNA which is protected from digestion by said enzyme;
 c. contacting said first library of subtracter DNA and said second library of tester DNA to obtain a mixture containing double-stranded hybrid DNA which include susceptible hybrid DNAs;
 d. treating said mixture with said enzyme to digest said susceptible hybrid DNAs, to obtain a treated mixture containing nicked-and-gapped hybrid DNAs; and
 e. further treating said treated mixture to digest said nicked-and-gapped hybrid DNAs, to obtain a resultant mixture containing digestion-resistant hybrid DNA which is enriched in tester DNA that is not present in said library of subtracter DNA;
 f. whereby said method provides an isolation of desired different sequences from said two DNA libraries.

46. The method as defined in claim 45, further comprising the step of repeating steps (c) through (e) on said enriched library at least one time.

47. The method as defined in claim 45, further comprising the step of amplifying said enriched library.

48. The method as defined in claim 45, wherein said subtracter DNA is nucleotide analog-containing subtracter DNA.

49. The method as defined in claim 45, wherein said enzyme is nucleotide analog-removing enzyme.

50. A kit for performing improved subtractive hybridization, comprising:
 a. a subtracter DNA library which is susceptible to digestion by an enzyme;
 b. a tester DNA library which is protected from digestion by said enzyme;
 c. said enzyme which can generate partial single-strand regions in susceptible DNA; and
 d. a treatment material which can digest nicked-and-gapped hybrid DNAs;
 e. whereby said kit can be used to provide an isolation of desired different sequences from said two DNA libraries.

51. The kit as defined in claim 50, further comprising a template-dependent extension activity.

52. The kit as defined in claim 50, further comprising an enzyme buffer.

53. The kit as defined in claim 50, further comprising a nuclease buffer.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:1:

GCCACCAGAA GAGCGTGTAC GCCA    24

( 2 ) INFORMATION FOR SEQ ID NO:2:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic DNA"

( x i ) SEQUENCE DESCRIPTION: SEQ ID NO:2:

GATCTGGCGT AC    12

( 2 ) INFORMATION FOR SEQ ID NO:3:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic uracil-containing
                DNA"

( x i ) SEQUENCE DESCRIPTION: SEQ ID NO:3:

CGGUAGUGAC UCGGUUAAGA UCGA    24

( 2 ) INFORMATION FOR SEQ ID NO:4:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic uracil-containing
                DNA"

( x i ) SEQUENCE DESCRIPTION: SEQ ID NO:4:

GAUCUCGAUC UU    12

( 2 ) INFORMATION FOR SEQ ID NO:5:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic DNA"

( x i ) SEQUENCE DESCRIPTION: SEQ ID NO:5:

GCCACCAGAA GAGCGTGTAC GTCC    24

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

CGGGACGTAC A         11

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic uracil-containing DNA"

(xi) SEQUENCE DESCRIPTION: SEQ ID NO:7:

CGGUAGUGAC UCGGUUAAGA UCGC         24

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic uracil-containing DNA"

(xi) SEQUENCE DESCRIPTION: SEQ ID NO:8:

CGGCGAUCUU A         11